US006306646B1

United States Patent
Saad et al.

(10) Patent No.: US 6,306,646 B1
(45) Date of Patent: Oct. 23, 2001

(54) CULTURE DISH

(75) Inventors: Bashar Saad, Greifensee; Tilo Callenbach, Jona, both of (CH)

(73) Assignee: Weidman Plastics Technology AG, Rapperswill (CH)

( * ) Notice: Subject to any disclaimer, the term of this patent is extended or adjusted under 35 U.S.C. 154(b) by 0 days.

(21) Appl. No.: 09/623,398

(22) PCT Filed: Dec. 22, 1998

(86) PCT No.: PCT/CH98/00549

§ 371 Date: Oct. 18, 2000

§ 102(e) Date: Oct. 18, 2000

(87) PCT Pub. No.: WO99/45096

PCT Pub. Date: Sep. 10, 1999

(30) Foreign Application Priority Data

Mar. 3, 1998 (CH) .................................... 506/98

(51) Int. Cl.⁷ .................................................. C12M 1/22
(52) U.S. Cl. .................................. 435/305.1; 435/305.2; 422/102
(58) Field of Search ...................... 422/102; 435/288.3, 435/288.4, 288.5, 305.1, 305.2, 305.3

(56) References Cited

U.S. PATENT DOCUMENTS

| 4,939,151 | | 7/1990 | Bacehowski et al. . |
| 4,977,078 | * | 12/1990 | Niimura et al. ......................... 435/7 |
| 5,041,266 | * | 8/1991 | Fox ....................................... 422/102 |
| 5,272,084 | * | 12/1993 | O'Connell et al. ........... 435/240.243 |
| 5,324,591 | | 6/1994 | Georger, Jr. et al. ................ 435/552 |
| 5,512,480 | * | 4/1996 | Sandstrom et al. ............... 435/289.1 |
| 5,792,653 | | 8/1998 | Weibezahn et al. ............... 435/288.5 |
| 6,027,695 | * | 2/2000 | Oldenburg et al. .................. 422/102 |
| 6,040,171 | * | 3/2000 | Ho et al. ............................ 435/288.1 |

FOREIGN PATENT DOCUMENTS

WO 96/03094 * 2/1996 (WO) .

* cited by examiner

Primary Examiner—David A. Redding
(74) Attorney, Agent, or Firm—Sughrue, Mion, Zinn, Macpeak & Seas, PLLC

(57) ABSTRACT

The invention relates to a culture dish consisting of a plastic material and intended for growing cell and tissue cultures (6). The growth surface (5) has a micro-structure and raised areas (9) whose height (A) is less than 110 micrometres and preferably less than approximately 100 micrometres. The micro-structure (8) of the growth surface increases the cell yield, with adherent cells being both optically easily accessible and readily harvested.

13 Claims, 1 Drawing Sheet

CULTURE DISH

Figure 1:
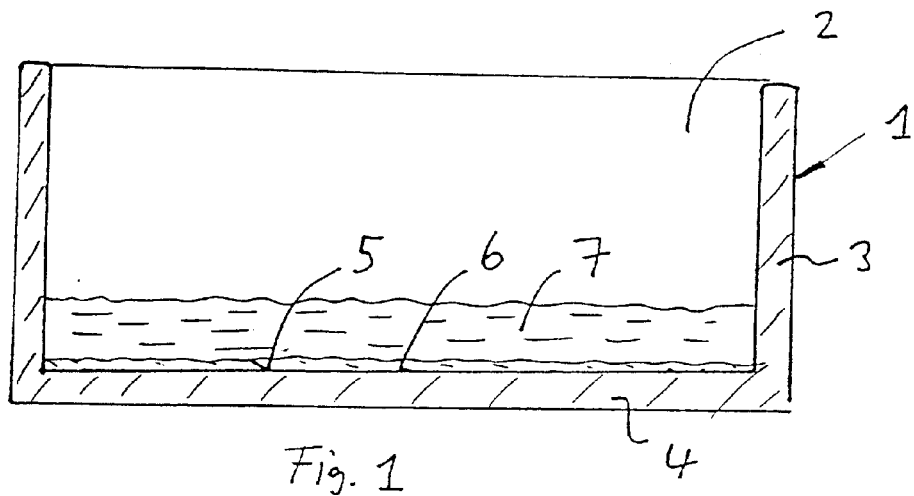

The invention relates to a culture vessel made of plastic for growing cell and tissue cultures according to the preamble of claim 1. Such vessels have been known for a long time for plant and animal cell cultures. In the past, glass bottles and dishes were primarily used. For one-time use, culture vessels made particularly of thermoplastic materials, e.g., polystyrene, have proven successful. Due to their normally hydrophobic surface, such polystyrene vessels are irradiated, for example, with gamma rays. The culture vessel can be, for example, a Petri dish, a multidish or, for example, also a microtiter plate or a microtest plate. Such culture vessels are described, for instance, in the publication by Lindl and J. Bauer, "Zell- und Gewebekultur" [Cell and Tissue Culture], 3rd Edition, Gustav Fischer Verlag (1994).

Also known are culture vessels whose growing surface is enlarged by elevations. This makes it possible to increase the cell yield 1.7 to 2-fold. Examples of such culture vessels may be found in the publication by Sigma, No. C 5934, of 1998. These vessels, however, present the problem that they substantially complicate microscopic examination. They also make harvesting of the adherent cells more difficult. EPO 552 412 A and EPO 614 967 A show culture vessels that are made as bottles and are respectively provided with a growing surface that has grooves as indentations and ribs as elevations. The distribution of cell and tissue cultures on the ribs is such that microscopic examination is not optimal. Furthermore, the grooves isolate cultures from one another, which adversely affects growth.

The object of the invention is to create a culture vessel of the cited type in which the cells are optically better accessible, are easier to harvest, and which at the same time provides a better cell yield and is nevertheless cost-effective in production.

This object is attained in a generic culture vessel according to claim 1. Due to this microstructure of the growing surface, the growing surface, but not the volume of the culture medium, is enlarged. Such a microstructure does not complicate harvesting of the adherent cells, nor is microscopic examination made more difficult, since the surface of the cell vessel is substantially flat. Also essential is that these microstructures provide an "in-vivo like" microenvironment for the growing adherent cells. This should substantially contribute to maintaining the state of differentiation and increasing the cell yield.

According to a further embodiment of the invention, the growing surface is provided with elevations and indentations whose height is less than about 100 micrometers. These elevations and indentations are preferably produced in an injection molding process. This type of process makes it possible to produce such elevations having a height of only about 5 nanometers. Preferably, these elevations are regularly arranged and identically shaped. If these elevations are made in the form of truncated pyramids, according to a further embodiment of the invention, regular, flat upper and lower surfaces as well as inclined surfaces are created on which the cells can grow. Since these elevations are very small, the cells are nevertheless situated on substantially the same optical plane for optical examination. In a culture vessel according to the invention, the elevations or indentations are therefore not statistically and randomly distributed but regularly arranged. This also makes it possible to create and test different microstructures for different cell cultures.

Figure 2:
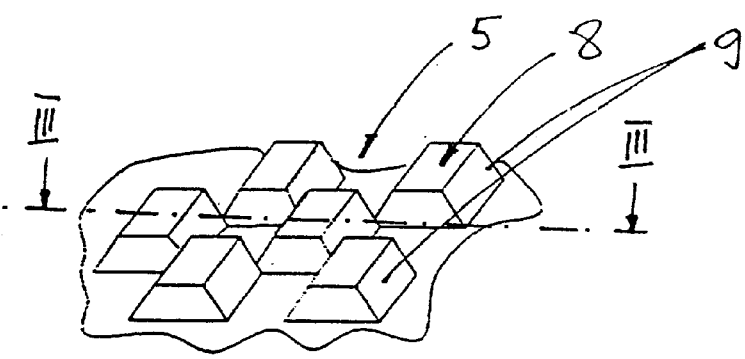
Figure 3:
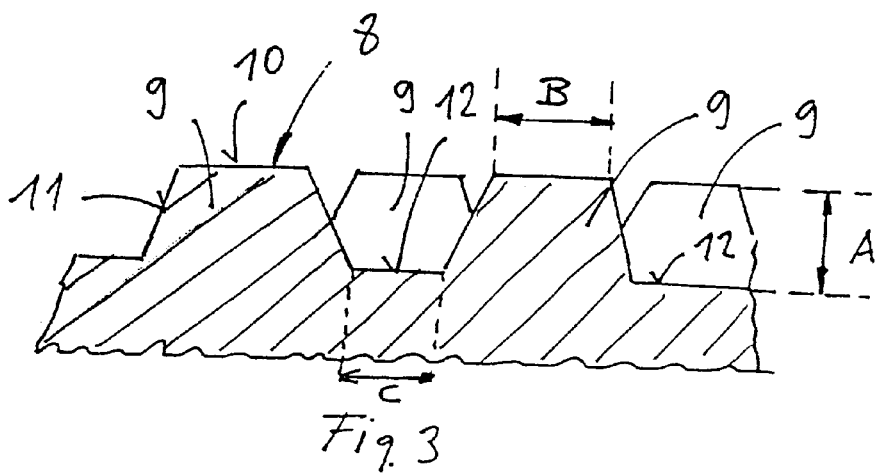

An exemplary embodiment of the invention will now be explained in greater detail by means of the drawing in which:

FIG. 1 is a schematic section through a culture vessel according to the invention with a cell monolayer in a nutrient solution, FIG. 2 is a strongly magnified view of an area of the growing surface, and FIG. 3 is a section along line III—III of FIG. 2.

FIG. 1 shows a culture vessel 1, which in this case is a Petri dish in which the cover is left off. The vessel 1 has a vessel wall 3 as well as a bottom 4 and forms an interior space 2 to receive a nutrient solution 7 as well as a cell culture 6. The upper side of the bottom 4 forms a growing surface 5, which is substantially flat as shown, and on which the cell culture 6 is located in nutrient solution 7. The cell culture 6 may also be a plant or animal cell culture. The vessel 1 is made of a thermoplastic, preferably polystyrene, and is produced by an injection molding process.

The growing surface 5 has a microstructure 8, a segment of which is shown in FIG. 2. The microstructure 8 preferably extends over the entire growing surface 5. Also feasible, however, is an embodiment in which only partial areas of the growing surface 5 have such a microstructure 8. The microstructure 8, as shown, consists of a plurality of elevations 9, which are preferably arranged in a regular pattern. According to FIG. 2, these elevations are truncated pyramids. Elevations of different shapes are also feasible, however; for instance, these elevations 9 can also have the shape of truncated cones. The elevations 9 have flat upper surfaces 10, preferably inclined lateral surfaces 11 and lower surfaces 12. These surfaces, as shown, are geometrically regular surfaces, preferably rectangular surfaces.

Height A of elevation 9 shown in FIG. 3 is preferably equal to or less than 100 micrometers. The preferred height A ranges from 10 to 60 micrometers. In this range, the microscope can be sharply focused and advantageous growth conditions exist. Height A can also be substantially smaller, however, for example 5 nanometers. Width B of surfaces 10 is preferably less than 300 micrometers. The width of the lateral faces 11 is also less than 300 micrometers. These surfaces 10 and 11 can be very small and can, for example, have a width of about 5 nanometers. Such microstructures are preferably produced by means of an injection molding process. The mold of the injection molding apparatus is then provided with a corresponding area having such a microstructure.

The size of the cells to be grown varies greatly. As a rule, the microstructure 8 is formed such that the cells grow on surfaces 10, 11 and 12. The cells can therefore typically also grow between the elevations 8 [sic]. However, the cells can also have a size comparable to that of the elevations 9. The cells can also be substantially larger than the elevations 8 [sic]. For optimal cell adhesion and cell growth, the culture vessel is treated, for example, in a microwave plasma.

What is claimed is:

1. A culture vessel made of plastic for growing cell and tissue cultures (6), with a growing surface that is provided with a microstructure (5) having elevations (9), whose height (A) is less than 110 micrometers, and indentations, whose bottom surface is a flat surface (12), characterized in that the elevations (9) each have an upper flat surface (10), and that said flat surfaces (12) are arranged between the elevations (9), and that adjacent indentations are connected with one another, wherein the elevations (9) are truncated pyramids or cones.

2. Culture vessel as claimed in claim 1, characterized in that the height (A) is less than 100 micrometers and preferably 10 to 60 micrometers.

3. Culture vessel as claimed in claim 1, characterized in that the flat surface (10) has a width (B) that is smaller than 300 micrometers.

4. A culture vessel as claimed in claim 2, wherein the flat surfaces (12) between the elevations (9) each have a width (C) or length that is smaller than 300 micrometers.

5. A culture vessel as claimed in claim 1, wherein the elevations (9) each have several lateral surfaces (11) which are inclined in relation to or extend perpendicularly from the flat surfaces (12) and are a part of said growing surface (5).

6. Culture vessel as claimed in claim 1, wherein it is produced from a thermoplastic by means of an injection molding process.

7. Culture vessel as claimed in claim 1, wherein it is made from an amorphous thermoplastic.

8. Culture vessel as claimed in claim 7, characterized in that the thermoplastic is polystyrene.

9. Culture vessel as claimed in claim 1, wherein it is surface treated for optimal cell adhesion and cell growth, for example, in a microwave plasma.

10. Culture vessel as claimed in claim 1, wherein the growing surface (5) has regularly arranged elevations (9) and these elevations (9) have geometric and defined surfaces (10, 11, 12).

11. Culture vessel as claimed in claim 1, wherein all or a substantial part of the elevations (9) are identical in shape.

12. A culture vessel as claimed in claim 1, wherein the growing surface (5) includes said flat surfaces (12), wherein said flat surfaces (12) are identical and regularly arranged between the elevations (9).

13. A culture vessel as claimed in claim 12, characterized in that said flat surfaces (12) between the elevations (9) are flat and rectangular.

* * * * *